United States Patent [19]

Cesa et al.

[11] Patent Number: 5,072,024

[45] Date of Patent: Dec. 10, 1991

[54] SYNTHESIS OF N-SUBSTITUTED AMIDES BY CONDENSATION OF NITRILES WITH CERTAIN ORGANIC HYDROXYL COMPOUNDS

[75] Inventors: Mark C. Cesa, South Euclid; Sandra L. Denman, Brunswick, both of Ohio

[73] Assignee: The Standard Oil Company, Cleveland, Ohio

[21] Appl. No.: 515,968

[22] Filed: Apr. 27, 1990

[51] Int. Cl.$^5$ ............................................. C07C 231/00
[52] U.S. Cl. ................................... 564/130; 564/124; 564/131; 564/184; 564/204; 564/215; 260/404; 502/202; 502/208; 502/217
[58] Field of Search ............ 564/124, 125, 126, 130, 564/131, 153, 156, 158, 159, 160, 170, 172, 123, 173, 174, 176, 177, 184, 204, 215; 502/202, 208, 217; 558/392, 414, 415, 428, 429, 430, 431, 432, 433, 445; 260/404

[56] References Cited

U.S. PATENT DOCUMENTS

| | | | |
|---|---|---|---|
| Re. 28,288 | 12/1974 | Goetz et al. | 260/404 |
| 2,601,387 | 11/1948 | Gresham et al. | 564/125 |
| 2,719,176 | 9/1955 | Coover, Jr. et al. | 564/124 |
| 2,742,501 | 4/1956 | Kleine et al. | 564/124 |
| 3,751,465 | 8/1973 | Takahashi et al. | 564/130 |
| 3,911,009 | 10/1975 | Yoshimura et al. | 564/127 |
| 3,948,989 | 4/1976 | Drake | 564/124 |

*Primary Examiner*—Glennon H. Hollrah
*Assistant Examiner*—Scott C. Rand
*Attorney, Agent, or Firm*—C. S. Lynch; M. F. Esposito; L. W. Evans

[57] ABSTRACT

Disclosed is a method which comprises the reaction in a reaction zone of a nitrile, RCN, with a hydroxyl compound, R'OH, in the presence of an inorganic catalyst introduced into the reaction zone, thereby producing a reaction mixture containing at least one amide selected from R—CONHR' and R—CON(R')$_2$, wherein each of R and R' contains no acetylenic unsaturation and 1 to 30 carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl, wherein said inorganic catalyst is selected from phosphates and sulfates of Be, Ng, Al and B, and mixtures thereof.

8 Claims, No Drawings

SYNTHESIS OF N-SUBSTITUTED AMIDES BY CONDENSATION OF NITRILES WITH CERTAIN ORGANIC HYDROXYL COMPOUNDS

This invention relates to the synthesis of N-substituted amides by condensation of nitriles with certain organic hydroxyl compounds. In particular, the invention relates to such a process using certain inorganic acids as catalysts for such reaction.

The important solvent, dimethylacetamide, is currently prepared industrially from acetic acid and dimethylamine. It is a superior organic solvent, with high boiling range and good thermal stability relative to other amides such as dimethylformamide. The current DMAC synthesis suffers from relatively high raw material costs. As a result, DMAC has a high price (about $1.00 per pound). This high price precludes use of DMAC in many applications where relatively inferior but lower priced solvents are used.

The process of the present invention has the potential to lower N-substituted amides production costs substantially because of the much lower prices of the starting materials compared with the price of the raw materials of the current synthetic method, thus offering the potential for growth of DMAC demand into applications where its superior properties would be an advantage.

It is an object of the present invention to provide an improved process of making N-substituted amides.

It is a further object of the invention to lower the cost of making N-substituted amides by condensing nitriles with alcohols in the presence of certain acidic catalysts.

Other objects, as well as aspects and advantages, of the invention will become apparent from a study of the specification, including the specific examples and the claims.

The foregoing and other objects are realized by the present invention according to which there is provided a method which comprises the reaction in a reaction zone of a nitrile, RCN, with a hydroxyl compound, R'OH, in the presence of an inorganic catalyst introduced into the reaction zone, thereby producing a reaction mixture containing at least one amide selected from R-CONHR' and R-CON(R')$_2$, wherein each of R and R' contains no acetylenic unsaturation and 1 to 30 (usually 1 to 12) carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl, wherein said inorganic catalyst is selected from phosphates and sulfates of Be, Mg, B and Al, and mixtures thereof.

Optimum catalyst amounts can be determined by routine experiments, but often vary from 0.0001 to 10 moles introduced into the reaction zone per 100 moles of the nitrile, RCN, introduced into the reaction zone. More usually the amount is from 0.01 to 5 moles per 100 moles of the nitrile, RCN.

In the process of the present invention a number of side reactions occur, producing numerous by-products in addition to the N-substituted amides, R-CONHR' and R-CON(R')$_2$. Typically, such by-products include mono-, di- and trimethyl amines, methyl acetate, water, acetic acid, and acetamide, where the charge reactants are acetonitrile and methanol, for instance.

In one aspect of practising the invention we contemplate recycling the reactor effluent to the reaction zone after first removing the R-CON(R')$_2$ product, acetic acid and possibly, water. This recycle stream is augmented by fresh RCN and R'OH feed to the reaction zone. This recycle procedure increases the overall yield and selectivity to R-CON(R')$_2$ based on fresh RCN charged to the reaction zone.

In another aspect of the invention we contemplate charging to the reaction zone a crude cut from the effluent of an ammoxidation reaction for making acrylonitrile, for instance, from propylene or from propane. Thus, a partially purified acetonitrile cut separated from the ammoxidation reactor effluent can be all or part of the acetonitrile charge to the reaction zone of this invention. This cut is mainly acetonitrile and water, but also contains small amounts of other components such as acrylonitrile, methacrylonitrile, propionitrile, pyridine, methyl-substituted pyridine(s), oxazole, pyrazine, benzonitrile, cyanopyridine, cyano-furans and aniline.

The condensation of nitriles with alcohols to form N-substituted amides is known as the Ritter reaction. Typical Ritter reaction catalysts are mineral acids, such as $H_2SO_4$ or $H_3PO_4$. The Ritter reaction is usually thought of as a reaction between a nitrile and a secondary or tertiary alcohol, which can readily form a carbonium ion in the presence of mineral acid. The carbonium ion then reacts with the nitrile in the key step in amide formation. See, for example, W. F. Gresham and W. E. Grigsby, U.S. Pat. No. 2,601,387.

Formation of amides from nitriles and primary alcohols, e.g. methanol, requires more severe conditions. A series of patents to Asahi (U.S. Pat. No. 3,751,465; JP 73 03,813; GB 1,229,618, Chemical Abstracts 74, 124883n and 76, 139955c) describe the use of catalysts such as transition metal salts for synthesis of DMAC from acetonitrile and methanol at high temperatures (up to 400° C. or higher) in stirred autoclaves.

According to the present invention, the present catalyzed synthesis of amides from nitriles and alcohols can be carried out in either the vapor phase or in the liquid phase, at atmospheric pressure or reduced or elevated pressure, in a batch mode, flow mode or continuous stirred reactor mode. If byproduct recycle is desired, the recycle process can be carried out continuously or in a batch mode. In an especially effective embodiment of the invention, applied to the synthesis of, for example, N,N-dimethylacetamide (DMAC) from acetonitrile and methanol, a continuous stirred reactor system can be used in which reaction byproducts and unreacted starting materials (recovered by distillation) are recycled to the reaction zone with fresh starting materials, with flows balanced so that an essentially constant DMAC synthesis rate is established with essentially no net byproduct synthesis.

The presence of inert diluents for any of the starting materials is within the scope of the invention. For example, the use of nitrogen or other inert gas in the reaction zone is permitted, and is favored in high-temperature liquid phase conditions to minimize unwanted side reactions. Also, the use of inert solvents with the reactants such as, for example (but not restricted to), alkanes and aromatic hydrocarbons is within the scope of the invention.

The reactants can be employed from the beginning of the reaction in the full amounts required for the reaction, or the reactants can be introduced to the reaction zone successively or stepwise during the course of the reaction.

It has also been found that water can improve N,N-disubstituted amide yield or selectivity in the present catalyzed reaction. When water is used it is used in the amount of up to 10 moles, usually no more than 2 moles, introduced into the reaction zone, per mole of RCN introduced into the reaction zone.

The process of this invention can be carried out at from 20° to 600° C. Optimum temperatures depend on the particular reactants and other parameters easily determined by routine test. For instance, primary alcohols usually require higher temperatures than secondary and tertiary alcohols.

Pressures can range from 0.1 atmosphere to 200 atmospheres or more. In liquid phase runs carried out in pressure vessels with low-boiling reactants, high reaction temperatures required for sufficient reaction rates result in pressures well above 1 atmosphere, as in the case of the specific examples herein.

The alcohol/nitrile mole ratio can range from 0.1 to 20, but usual ratios range from 1.0 to 10. Lower amounts of alcohol relative to nitrile result in promotion of formation of N-monosubstituted amide, and higher amounts sometimes can alcoholyze amide products, lowering yield of desired product. It should be noted that formation of appreciable amounts of N-monosubstituted amide is not necessarily a disadvantage. First, if this is desired as a co-product, or in the second instance if a recycle process be used. In the latter event the N-substituted amide is a very efficacious feed to the reaction zone, where it helps maintain the equilibrium between this by-product and all other reaction products.

The process of the present invention does not involve the intentional addition of molecular oxygen into the reaction zone, because of loss of product by oxidation.

The following examples of the invention are exemplary and should not be taken as in any way limiting.

EXAMPLE 1

A mixture of acetonitrile (40.64 g, 0.9900 mol), methanol (41.86 g, 1.3064 mol), and BPO$_4$ (3.19 g, 0.0302 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 350° C., and the reaction mixture was stirred at that temperature for 3.5 hours. The reactor was then cooled, and the reaction mixture was analyzed by gas chromatography. Conversion of methanol was 86.8% and conversion of acetonitrile was 89.4%. Product yields (based on acetonitrile) were as follows: methylamine 0.5%, dimethylamine 9.7%, methyl acetate 3.3%, N,N-dimethylacetamide (DMAC) 26.4%, acetic acid 18.4%, N-methylacetamide 30.6%, and acetamide 12.8%.

COMPARATIVE EXAMPLE A

A mixture of acetonitrile (42.15 g, 1.027 mol) and methanol 2.77 g, 1.335 mol) was placed in a stainless steel autoclave of 300 mL internal volume. The reactor was sealed, and the reaction mixture was purged with nitrogen through a dip tube for 30 minutes. The reactor was then heated to 360° C., and the reaction mixture was stirred vigorously. The temperature of the reaction mixture reached 360° C., and the reaction mixture was stirred at that temperature for 1.0 hours. The reactor was then cooled, and the reaction mixture was analyzed by gas chromatography. Conversion of methanol was 18.2% and conversion of acetonitrile was 14.6%. Product yields (based on acetonitrile) were as follows: methylamine 0.4%, dimethylamine 0%, methyl acetate 3.0%, N,N-dimethylacetamide (DMAC) 0.04, acetic acid 0.1%, N-methylacetamide 0.3%, and acetamide 1.86%.

COMPARATIVE EXAMPLE B

A mixture of acetonitrile (41.05 g, 0.9999 mol) and methanol (41.64 g, 1.2995 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 328° C., and the reaction mixture was stirred at that temperature for 3 hours. The reactor was then cooled, and the reaction mixture was analyzed by gas chromatography. Conversion of methanol was 37.1% and conversion of acetonitrile was 20.0%. Product yields (based on acetonitrile) were as follows: methylamine 2.2%, dimethylamine 7.2%, methyl acetate 11.5%, N,N-dimethylacetamide (DMAC) 0.7%, acetic acid 0.6%, N-methylacetamide 5.4%, and acetamide 5.5%.

COMPARATIVE EXAMPLE C

A mixture of acetonitrile (31.57 g, 0.7690 mol) and methanol (32.04 g, 0.9999 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 353° C.; and the reaction mixture was stirred at that temperature for 4 hours. The reactor was then cooled, and the reaction mixture was analyzed by gas chromatography. Conversion of methanol was 37.8% and conversion of acetonitrile was 20.4%. Product yields (based on acetonitrile) were as follows: methylamine 2.6%, dimethylamine 5.6%, methyl acetate 12.2%, N,N-dimethylacetamide (DMAC) 0.5%, acetic acid 0.3%, N-methylacetamide 3.3%, and acetamide 4.1%.

EXAMPLE 2

To simulate recycle conditions, a mixture of acetonitrile (12.1 g, 0.2947 mol), methanol (19.87 g, 0.6201 mol), BPO$_4$ (3.21 g, 0.0303 mol), methyl acetate (0.96 g, 0.0130 mol), acetic acid (6.65 g, 0.1107 mol), N-methylacetamide (29.1 g, 0.398 mol), and acetamide (11.69 g, 0.1979 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 370° C., and the reaction mixture was stirred for 2 hours. The reactor was then cooled, and the reaction mixture was analyzed by gas chromatography. Conversion of methanol was 86.6% and conversion of acetonitrile was 82.2%. N,N-dimethylacetamide yield (based on acetonitrile) was 56.2%.

EXAMPLE 3

A mixture of acetonitrile (41.05 g, 0.9999 mol), methanol (41.65 g, 1.2999 mol), and AlPO$_4$ (3.66 g, 0.0300 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 397° C., and the reaction mixture was stirred for 2 hours at that temperature. The reactor was then cooled, and the reaction mixture was analyzed by gas chromatography. Conversion of methanol was 96.5% and conversion of acetonitrile was 83.4%. Product yields (based on acetonitrile) were as follows: methylamine 1.9%, dimethylamine 7.7%, methyl acetate 0.4%, N,N-dimethylacetamide (DMAC) 23.2%, acetic acid 11.6%, N-methylacetamide 27.8%, and acetamide 31.7%.

EXAMPLE 4

To simulate recycle conditions, a mixture of acetonitrile (12.19 g, 0.2969 mol), methanol (19.50 g, 0.6086 mol), AlPO$_4$ (2.98 g, 0.0244 mol), methylamine (0.95 g, 0.0306 mol), dimethylamine (3.93 g, 0.0872 mol), methyl acetate (0.37 g, 0.0050 mol), acetic acid (7.10 g, 0.1182 mol), N-methylacetamide (20.33 g, 0.2781 mol), and acetamide (13.84 g, 0.2343 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 380° C., and the reaction mixture was analyzed by gas chromatography. Conversion of methanol was 90.9% d and conversion of acetonitrile was 77.2%. N,N-dimethylacetamide yield (based on acetonitrile) was 74.7%.

EXAMPLE 5

A mixture of acetonitrile (1.28 mol), methanol (2.75 mol), and BPO$_4$ (0.109 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 240° C., and the reaction mixture was stirred for 1 hour at that temperature. The reactor was then cooled, and the reaction mixture was analyzed by gas chromatography. Conversion of methanol was 78% and conversion of acetonitrile was 94%. Product yields (based on acetonitrile) were as follows: methyl acetate 11.4%, N,N-dimethylacetamide (DMAC) 7.5%, N-methylacetamide 28.3%, and acetamide 16.6%.

EXAMPLE 6

A mixture of acetonitrile (1.41 mol), methanol (2.82 mol), and AlPO$_4$ (0.0947 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 250° C., and the reaction mixture was stirred for 1.25 hours at that temperature. The reactor was then cooled, and the reaction mixture was analyzed by gas chromatography. Conversion of methanol was 7.1% and conversion of acetonitrile was 7.1%. Product yields (based on acetonitrile) were as follows: methyl acetate 2.0%, N,N-dimethylacetamide (DMAC) trace, acetic acid trace, N-methylacetamide 0.31%, and acetamide 1.9%.

EXAMPLE 7

A mixture of acetonitrile (1.40 mol), methanol (2.80 mol), and MgSO$_4$ (0.1035 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 240° C., and the reaction mixture was stirred for 4 hours and 25 minutes at that temperature. The reactor was then cooled, and the reaction mixture was analyzed by gas chromatography. Conversion of methanol was 10% and conversion of acetonitrile was 19%. Product yields (based on acetonitrile) were as follows: methyl acetate 0.75%, N,N-dimethylacetamide (DMAC) trace, acetic acid trace, N-methylacetamide trace, and acetamide 0.48%.

EXAMPLE 8

A mixture of acetonitrile (1.75 mol), methanol (3.38 mol), and aluminum sulfate hydrate (0.0782 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 240° C., and the reaction mixture was stirred for 3 hours and 55 minutes at that temperature. The reactor was then cooled, and the reaction mixture was analyzed by gas chromatography. Conversion of methanol was 11% and conversion of acetonitrile was 58%. Product yields (based on acetonitrile) were as follows: methyl acetate 20%, N,N-dimethylacetamide (DMAC) trace, acetic acid 0.57%, N-methylacetamide 0.57%, and acetamide 0.85%.

EXAMPLE 9

A mixture of acetonitrile (0.725 mol), methanol (1.44 mol), BPO$_4$ (0.103 mol), and MgSO$_4$ (0.142 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 250° C., and the reaction mixture was stirred for 4 hours at that temperature. The reactor was then cooled, and the reaction mixture was analyzed by gas chromatography. Conversion of methanol was 68% and conversion of acetonitrile was 74%. Product yields (based on acetonitrile) were as follows: methyl acetate 21%, N,N-dimethylacetamide (DMAC) 2.7%, acetic acid 4.4%, N-methylacetamide 18%, and acetamide 17%.

COMPARATIVE EXAMPLE D

A mixture of acetonitrile (1.05 mol), methanol (2.94 mol), and cadmium acetate (0.0102 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 260° C., and the reaction mixture was stirred for 5.75 hours at that temperature. The reactor was then cooled, and the reaction mixture was analyzed by gas chromatography. Conversion of methanol was 34% and conversion of acetonitrile was 27%. Product yields (based on acetonitrile) were as follows: methyl acetate 12%, N,N-dimethylacetamide (DMAC) trace, acetic acid trace, N-methylacetamide 1.4%, and acetamide 4.8%.

EXAMPLE 10

A stainless steel upward flow tube microreactor was charged with $BPO_4$ (ground to 40 mesh, 2.29 g, 3 mL) and immersed in a molten salt bath at 300° C. While $N_2$ was fed through the reactor at a flow rate of 30 mL/min (measured at room temperature and atmospheric pressure), a 2.45/1molar mixture of methanol and acetonitrile was fed over the catalyst at a flow rate corresponding to a liquid contact time of 1.38 sec. The reactor effluent was passed through an ice-cooled scrubber containing water. After 99.00 mmol of methanol and 40.50 mmol of acetonitrile were reacted in the above manner, the contents of the scrubber were analyzed by gas-chromatography. Methanol conversion was 32% and acetonitrile conversion was approximately 1%. Product yields were as follows: methyl acetate 0.62%, N,N-dimethylacetamide O, acetic acid 0.5%, N-methylacetamide 0.064%, and acetamide 0.27%.

EXAMPLE 11

A mixture of acetonitrile (0.6156 mol), ethanol (0.8001 mol), and $BPO_4$ (0.0184 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 362° C., and the reaction mixture was stirred for 4 hours at that temperature. The reactor was then cooled, and the reaction mixture was analyzed by gas chromatography. Conversion of ethanol was 67.9% and conversion of acetonitrile was 47.9%. Product yields (based on acetonitrile) were as follows: ethyl acetate 14.1%, N,N-diethylacetamide 2.2%, acetic acid 3.5%, N-ethylacetamide 11.8%, and acetamide 32.9%.

COMPARATIVE EXAMPLE E

A mixture of acetonitrile (0.6195 mol) and ethanol (0.8001 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 364° C., and the reaction mixture was stirred for 4 hours at that temperature. The reactor was then cooled, and the reaction mixture was analyzed by gas chromatography. Conversion of ethanol was 36.2% and conversion of acetonitrile was 19.7%. Product yields (based on acetonitrile) were as follows: ethyl acetate 8.4%, N,N-diethylacetamide 0.1%, acetic acid 1.1%, N-ethylacetamide 0.6%, and acetamide 2.6%.

EXAMPLE 12

A mixture of acetonitrile (0.3765 mol), isopropyl alcohol (0.7501 mol), and $BPO_4$ (0.0100 mol) was placed in a stainless steel autoclave of 300 mL internal volume. The reactor was sealed, and the reaction mixture was purged with nitrogen through a dip tube for 30 minutes. The reactor was then heated and the reaction mixture was stirred vigorously. The temperature of the reaction mixture reached 370° C., and the reaction mixture was stirred for 5 hours at that temperature. The reactor was then cooled, and the reaction mixture was analyzed by gas chromatography. Conversion of isopropyl alcohol was 79.1% and conversion of acetonitrile was 40.5%. Product yields (based on acetonitrile) were as follows: isopropyl acetate 10.7%, acetic acid 25.7%, and N-isopropylacetamide 2.1%.

COMPARATIVE EXAMPLE F

A mixture of acetonitrile (0.0246 mol) and isopropyl alcohol (0.0496 mol) was placed in a tubular stainless steel pressure vessel of 12 mL internal volume. The reaction mixture was purged with nitrogen for 30 minutes, and the reactor was sealed. The reactor was then heated to 360° C. for 6 hours. The reactor was then cooled, and the reaction mixture was analyzed by gas chromatography. Conversion of isopropyl alcohol was 67.7% and conversion of acetonitrile was 35.0%. Product yields (based on acetonitrile) were as follows: isopropyl acetate 6.3%, acetic acid 11.7%, and N-isopropylacetamide 0.4%.

As will be evident to those skilled in the art various modifications of this invention can be made or followed in the light of the foregoing disclosure and discussion without departing from the spirit and scope of the disclosure or from the scope of the claims.

We claim:

1. A method which comprises the reaction in a reaction zone of a nitrile, RCN, with a hydroxyl compound, R'OH, in the presence of an inorganic catalyst introduced into the reaction zone, thereby producing a reaction mixture containing at least one amide selected from R-CONHR' and R-CON(R')$_2$, wherein
    each of R and R' contains no acetylenic unsaturation and 1 to 30 carbon atoms,
    each of R and R' is an independently selected hydrocarbyl group and,
    wherein said inorganic catalyst is selected from phosphates and sulfates of Be, Mg, Al and B, and mixtures thereof.

2. A method according to claim 1 which comprises the reaction in a reaction zone of acetonitrile with methanol, thereby producing a reaction mixture containing dimethylacetamide.

3. A method of claim 1 wherein water as a reaction promoter is introduced into the reaction zone in the amount of up to 10 moles per mole of RCN introduced into said reaction zone.

4. A method of claim 1 wherein water as a reaction promoter is introduced into the reaction zone in the amount of up to 2 moles per mole of RCN introduced into said reaction zone.

5. A method of claim 2 wherein water as a reaction promoter is introduced into the reaction zone in the amount of up to 10 moles per mole of RCN introduced into said reaction zone.

6. A method of claim 2 wherein water as a reaction promoter is introduced into the reaction zone in the amount of up to 2 moles per mole of RCN introduced into said reaction zone.

7. A method of claim 1 wherein each of R and R' contains no more than 12 C atoms.

8. A method of claim 3 wherein each of R and R' contains no more than 12 C atoms.

* * * * *